United States Patent
Amano et al.

(10) Patent No.: US 7,371,740 B2
(45) Date of Patent: May 13, 2008

(54) PHOSPHORYLATED GLYCERYL ETHER ALUMINUM SALT

(75) Inventors: Shinya Amano, Tochigi (JP);
Tomohiko Sano, Tokyo (JP);
Hiromitsu Kawada, Tokyo (JP);
Takashi Kawata, Tokyo (JP)

(73) Assignee: Kao Corporation, Tokyo (JP)

( * ) Notice: Subject to any disclaimer, the term of this patent is extended or adjusted under 35 U.S.C. 154(b) by 391 days.

(21) Appl. No.: 10/930,773

(22) Filed: Sep. 1, 2004

(65) Prior Publication Data
US 2005/0234023 A1    Oct. 20, 2005

(30) Foreign Application Priority Data
Sep. 5, 2003  (JP)  ............................. 2003-314212
Jun. 29, 2004 (JP)  ............................. 2004-190728

(51) Int. Cl.
*A61K 31/66*  (2006.01)
*C07F 9/02*   (2006.01)

(52) U.S. Cl. ......................................... 514/129; 556/24

(58) Field of Classification Search .................. 556/24; 514/129
See application file for complete search history.

(56) References Cited

U.S. PATENT DOCUMENTS

| | | |
|---|---|---|
| 4,510,070 A | 4/1985 | Tsutsumi et al. |
| 4,776,976 A * | 10/1988 | Nakamura et al. ............ 516/56 |
| 2004/0009140 A1 | 1/2004 | Nishijima et al. |

FOREIGN PATENT DOCUMENTS

| | | |
|---|---|---|
| EP | 0 719 541 A1 | 7/1996 |
| JP | 2001-192315 | 7/2001 |
| JP | 2002-187817 | 7/2002 |

\* cited by examiner

*Primary Examiner*—Rei-tsang Shiao
(74) *Attorney, Agent, or Firm*—Oblon, Spivak, McClelland, Maier & Neustadt, P.C.

(57) ABSTRACT

The present invention relates to a phosphorylated glyceryl ether aluminum salt represented by the general formula (1):

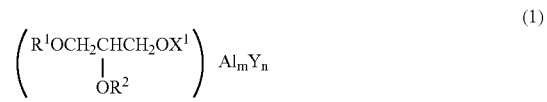

(wherein $R^1$ represents an alkyl or an alkenyl group with 8 to 32 carbon atoms; $R^2$ represents a hydrogen atom, a phosphoric acid residue or $-CH_2CH(OR^2)CH_2OR^1$ (wherein $R^1$ and $R^2$ are the same as described above, provided that a repeated binding number is 4 at the most when $R^2$ is $-CH_2CH(OR^2)CH_2OR^1$); $X^1$ represents a hydrogen atom or a phosphoric acid residue, and at least one of $X^1$ and $R^2$ is a phosphoric acid residue; Y represents an alkali metal atom or an alkaline earth metal atom; m represents a number from 0.3 to 1, and n represents a number from 0 to 1), and an external dermatological agent containing the same. The compound has benefits such as an excellent pore contracting activity and also a good solubility in oil.

5 Claims, No Drawings

PHOSPHORYLATED GLYCERYL ETHER ALUMINUM SALT

FIELD OF THE INVENTION

The present invention relates to a novel phosphorylated glyceryl ether compound and a composition of an external dermatological agent containing the same.

BACKGROUND OF THE INVENTION

Conspicuous pores on skin are listed at the higher rank of women's skin problems. Causes of conspicuous pores include, for example, clogged dirt and oil in the pores, pigmentary deposits and the shape of the opening of the hair pouch. As to the pore-clogging dirt and oil, various removing agents have been developed and used widely. Removal of the pore-clogging dirt and oil itself, however, is rather a drawback because pores on skin become more conspicuous unless the pore size is also decreased. Therefore, a contracting agent which makes pores inconspicuous by shrinking the pore itself has been demanded. From such point of view, phosphorylated glyceryl ethers have been known as compounds which significantly contract keratinocyte (JP-A1-2002-187817). In addition, the phosphorylated glyceryl ethers have been known to be ameliorating agents forskin elasticity (JP-A1-2001-192315).

As indicated by the presence of sebum and clogged dirt and oil in pores, the environment of pores is lipophilic. However, the above-described conventional phosphorylated glyceryl ethers are water-soluble. Therefore, a continued need exists for a compound which works more effectively on pores.

SUMMARY OF THE INVENTION

The present invention relates to a phosphorylated glyceryl ether aluminum salt represented by the general formula (1):

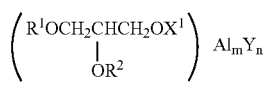

(1)

(wherein $R^1$ represents an alkyl or an alkenyl group with 8 to 32 carbon atoms; $R^2$ represents a hydrogen atom, a phosphoric acid residue or $-CH_2CH(OR^2)CH_2OR^1$ (wherein $R^1$ and $R^2$ are the same as described above, provided that a repeated binding number is 4 at the most when $R^2$ is $-CH_2CH(OR^2)CH_2OR^1$); $X^1$ represents a hydrogen atom or a phosphoric acid residue, and at least one of $X^1$ and $R^2$ is a phosphoric acid residue; Y represents an alkali metal atom or an alkaline earth metal atom; m represents a number from 0.3 to 1, n represents a number from 0 to 1), and a manufacturing method thereof.

Also, the present invention relates to a phosphorylated glyceryl ether aluminum salt obtained by a reaction of a phosphorylated glyceryl ether represented by the general formula (2):

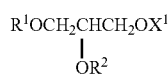

(2)

(wherein $R^1$ represents an alkyl or an alkenyl group with 8 to 32 carbon atoms; $R^2$ represents a hydrogen atom, a phosphoric acid residue or $-CH_2CH(OR^2)CH_2OR^1$ (wherein $R^1$ and $R^2$ are the same as described above, provided that a repeated binding number is 4 at the most when $R^2$ is $-CH_2CH(OR^2)CH_2OR^1$); $X^1$ represents a hydrogen atom or a phosphoric acid residue, and at least one of $X^1$ and $R^2$ is a phosphoric acid residue) with an aluminum compound, and a manufacturing method thereof.

Also, the present invention relates to a composition of an external dermatological agent containing a phosphorylated glyceryl ether aluminum salt represented by the above-described general formula (1), or a phosphorylated glyceryl ether aluminum salt obtained by the above described method and oily material.

And also, the present invention relates to a pore contracting agent and an ameliorating agent for skin elasticity containing a phosphorylated glyceryl ether aluminum salt represented by the above-described general formula (1), or a phosphorylated glyceryl ether aluminum salt obtained by the above-described method.

Further, the present invention relates to the use of a phosphorylated glyceryl ether aluminum salt represented by the above-described general formula (1), or a phosphorylated glyceryl ether aluminum salt obtained by the above-described method for the manufacture of a pore contracting agent and an ameliorating agent for skin elasticity.

Furthermore, the present invention relates to a method for ameliorating skin elasticity and/or for pore contraction, characterized in that a phosphorylated glyceryl ether aluminum salt represented by the above-described general formula (1), or a phosphorylated glyceryl ether aluminum salt obtained by the above-described method is applied to skin.

DETAILED DESCRIPTION OF THE INVENTION

The present inventors have searched for a compound superior insolubility in oil and pore contracting activity, and found that an aluminum salt of phosphorylated glyceryl ether has surprising benefits including excellent pore contracting activity and solubility in various oily components, and thus makes it possible to be stably compounded in an external dermatological agent containing oily material.

A compound of the present invention has benefits such as an excellent pore contracting activity and an ameliorating activity for skin elasticity; yet is highly soluble in oil, thus suitable for compounding in various external dermatological agents containing oily material.

In the general formula (1), the carbon number of an alkyl group or an alkenyl group represented by $R^1$ is 8 to 32, preferably 10 to 22, more preferably 16 to 20 is preferred. As to an alkyl group and an alkenyl group, an alkyl group is preferable. An alkyl group or an alkenyl group includes any of a straight chain or a branched chain type. Typically, an alkyl group includes n-decyl, trimethyldecyl, n-undecyl, 2-heptylundecyl, n-dodecyl, n-tridecyl, n-tetradecyl, n-pentadecyl, n-hexadecyl, n-heptadecyl, n-octadecyl, methylheptadecyl (isostearyl), n-nonadecyl, n-icosyl, n-docosyl, isotridecyl, isopalmityl, and the like. Among them, a branched alkyl group with 10 to 22 carbon atoms such as isotridecyl, isopalmityl, methylheptadecyl (isostearyl), 2-heptylundecyl is preferable. Isostearyl alcohol is obtained by reduction of isostearic acid which is produced as a by-product of the dimmer acid manufacturing process from beef tallow or soybean oil, or the like. Therefore, an isostearyl group is mostly a mixed group with a methyl branch at various positions on the main chains. Typical alkenyl groups include 10-undecenyl, 9-octadecenyl (oleyl), 9,12-octadienyl (linoleyl), 13-docosenyl groups, and the like.

$R^2$ represents a hydrogen atom, a phosphoric acid residue or —$CH_2CH(OR^2)CH_2OR^1$. Among them, a hydrogen atom is preferable.

$X^1$ represents a hydrogen atom or a phosphoric acid residue, within which a phosphoric acid residue is preferable. Y represents an alkali metal atom or an alkali earth metal atom. Among them, sodium, potassium, lithium and calcium are preferable, within which sodium and potassium are more preferable. In formula (1), m represents a number from 0.3 to 1 and n represents a number from 0 to 1.

In the general formula (1), a preferable conformation is that $R^2$ is a hydrogen atom and $X^1$ is a phosphoric acid residue. However, it should be noted that said compound sometimes contains a small amount of compounds having a phosphoric acid residue or —$CH_2CH(OR^2)CH_2OR^1$ for $R^2$. When $R^2$ is —$CH_2CH(OR^2)CH_2OR^1$, a repeated binding number is 4 at the most, and preferably 3 at the most.

A preferred compound (1) of the present invention, that is a salt of phosphorylated glyceryl ether and aluminum, may take a double salt form or a complex form. The ratio of phosphorylated glyceryl ether to aluminum may be 1:0.3 to 1. Further, compound (1) of the present invention may take a hydrate form.

Also, a part of a salt may be an alkali metal salt or an alkali earth metal salt such as a sodium salt. In the case of an alkali metal salt such as a sodium salt, may be from 0 to 1. Considering stability of a composition when said compound is incorporated in cosmetics or the like, n is preferably larger than 0.05. Considering easiness of manufacturing said compound, n is preferably smaller than 0.7. In addition, all or a part of the above-described metal salt may be a potassium salt, a calcium salt, or the like.

A preferred compound (1) of the present invention may be manufactured, for example, by the following reaction scheme:

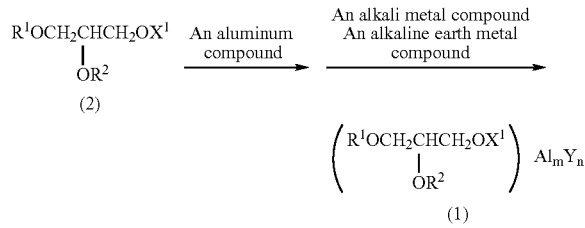

(wherein $R^1$, $R^2$, $X^1$, Y, m and n are the same as described above)

That is, a compound (1) of the present invention may be obtained by a reaction of phosphorylated glyceryl ether represented by the general formula (2) with an aluminum compound, followed by a reaction, if necessary, with an alkali metal compound such as a sodium compound or an alkaline earth metal compound.

Examples of the aluminum compounds used for said reaction include aluminum sulfate, aluminum nitrate, aluminum chloride, aluminum hydroxide, and the like. This reaction is carried out in an alcoholic solvent, for example, ethanol, isopropanol, and the like, with phosphorylated glyceryl ether (2) and an aluminum compound, at a temperature ranging from room temperature to 100° C. for 30 minutes to 50 hours, preferably for 30 minutes to 5 hours. Relative to 1 mole of phosphorylated glyceryl ether (2), a ratio of an aluminum compound is 0.3 and above, preferably 0.3 to 2 moles.

Among alkali metal compounds used for the reaction, a sodium compound includes sodium hydroxide, sodium carbonate, sodium bicarbonate, and the like. This reaction is carried out, for example, in a mixed solvent of toluene and alcohol, with phosphorylated glyceryl ether (2) and a sodium compound, at a temperature ranging from room temperature to 100° C. for 30 minutes to 50 hours, preferably for 30 minutes to 5 hours. Relative to 1 mole of phosphorylated glyceryl ether (2), a ratio of a sodium compound is 0 and above, preferably 0.05 to 0.7 moles. The potassium compounds include potassium hydroxide, potassium carbonate and the like, and the calcium compounds include calcium hydroxide and the like. The reaction can be carried out under the same condition as the reaction carried out with a sodium compound.

After the reaction, a compound of the present invention may be isolated easily by procedures such as washing and re-crystallization.

The present invention also provides a phosphorylated glyceryl ether aluminum salt which may be obtained by a reaction of phosphorylated glyceryl ether represented by the above general formula (2) with an aluminum compound, followed by a reaction, if necessary, with an alkali metal compound or an alkaline earth metal compound.

A compound (1) of the present invention may be used as a pore contracting agent and an ameliorating agent for skin elasticity, and is also formulated in an external dermatological agent, on account of its excellent pore contracting activity and ameliorating activity for skin elasticity. Further, a compound (1) of the present invention is soluble in various oily base materials, and therefore, may be stably compounded in external dermatological agents containing oily materials, especially with oily-material-containing cosmetic preparations for skin.

Such an external dermatological agent includes emulsified cosmetic, milky lotion, skin conditioner, cream, oily cosmetic, and the like. The external dermatological agent may be formulated properly with an oily base material such as plant oil, animal oil and synthetic oil, water, emulsifier, analgesic/antiphlogistic agent, analgesics, disinfectants, styptics, emollients, hormone preparations, vitamins, moisturizing agents, ultraviolet absorbents, alcohols, chelating agents, pH controlling agents, preservatives, thickening agents, pigments, perfumes, and the like, as long as the effects of the present invention is not restrained. Amount of a compound of the general formula (1) to be compounded in the above-described external dermatological agents is preferably 0.001 to 20% by weight, more preferably 0.01 to 5% by weight.

EXAMPLES

The following examples further describe and demonstrate embodiments of the present invention. The examples are given solely for the purpose of illustration and are not to be construed as limitations of the present invention.

Manufacturing Example 1

Manufacturing of 1-isostearylglycerol-3-phosphate aluminum salt (1):

To 150 mL of toluene, 47.4 g (0.459 mole) of 95% phosphoric acid was mixed and 50 g (0.153 mole) of isostearylglycidyl ether was added in drop-wise at room temperature for 30 minutes in a nitrogen atmosphere. After additional stirring for 2 hours, 50 g of distilled water and 25 g of isopropyl alcohol were added, and an aqueous layer was separated. The organic layer was washed by a 2.5% sodium sulfate solution and water sequentially, and then concentrated to obtain 72.1 g of crude 1-isostearylglycerol-3-phosphate.

Analysis by gel permeation chromatography (eluent: THF (tetrahydrofuran); detection: RI; area percentage) 1-isostearylglycerol-3-phosphate: 85.5% 1-isostearyl-2-(3'-isostearylglyceroyl)glycerol-3-phosphate: 12.8% 1-isostearyl-2-(3'-isostearyl-2'-(3"-isostearyl glyceroyl)glyceroyl)glycerol-3-phosphate: 1.7% IR (cm$^{-1}$, NaCl-disk method): 3296, 2928, 2860, 1466, 1380, 1120, 1022 $^1$H-NMR($\delta$, ppm, CDCl$_3$): 4.20-3.90 (m), 3.78-3.43 (m), 1.57 (s), 1.28-1.21 (s), 0.85 (s)

In ethanol 72.1 g of the above-obtained crude 1-isostearylglycerol-3-phosphate was dissolved, followed by the addition of a 19.3 g (0.0306 mol) of aluminum sulfate 14-18 hydrate solution dissolved in 85 g of water at 70° C. and stirred at 70° C. for 30 minutes. Subsequently, toluene and isopropyl alcohol were added to the reaction mixture, followed by separation of the aqueous layer, and washing of the organic layer with distilled water. The organic layer was added gradually to acetone cooled down to 10° C. or less to precipitate a white powder, which was washed with acetone and dried to yield 48.1 g of 1-isostearylglycerol-3-phosphate aluminum salt. In addition, said product was added to 50% sulfuric acid and the mixture was stirred for 30 minutes, followed by extraction with ether and removal of the solvent by evaporation to prepare a sample to be analyzed by means of gel permeation chromatography. From the analysis, the composition of glyceryl ether part of the product was found to be as follows.

Analysis by gel permeation chromatography (eluent: THF (tetrahydrofuran); detection: RI; area percentage) 1-isostearylglycerol-3-phosphate: 85.5% 1-isostearyl-2-(3'-isostearylglyceroyl)glycerol-3-phosphate: 12.8% 1-isostearyl-2-(3'-isostearyl-2'-(3"-isostearyl glyceroyl)glyceroyl)glycerol-3-phosphate: 1.7% IR (cm$^{-1}$, KBr-tablet method): 3424, 2928, 2860, 1470, 1380, 1124, 1060 Phosphorus content (elemental analysis): 6.3% Aluminum content (ICP analysis: inductively coupled plasma emission spectrometry): 2.6% m=0.5 n=0

Manufacturing Example 2

Manufacturing of 1-isostearylglycerol-3-phosphate aluminum salt (2):

In ethanol 505 g of crude 1-isostearylglycerol-3-phosphate obtained according to a similar procedure as in Manufacturing Example 1 was dissolved, followed by the addition of 174 g (0.276 mol) of a solution of aluminum sulfate 14-18 hydrate dissolved in 595 g of water at 70° C. and stirred at 70° C. for 30 minutes. Subsequently, toluene and isopropyl alcohol were added to the resultant solution, followed by separation of the aqueous layer and sequential washing of the organic layer with 39.2 g (0.467 mole) of sodium bicarbonate dissolved in 634.2 g of water and with 595 g of distilled water. The organic layer was added gradually to acetone cooled down to 10° C. or less to precipitate white powder, which was then washed with acetone and dried to yield 349 g of 1-isostearylglycerol-3-phosphate aluminum salt.

In addition, said product was added to 50% sulfuric acid and stirred for 30 minutes, followed by extraction with ether and removal of the solvent by evaporation to prepare a sample to be analyzed by means of gel permeation chromatography. From the analysis, the composition of the glyceryl ether part of the product was determined as follows. Analysis by gel permeation chromatography (eluent: THF (tetrahydrofuran); detection: RI; area percentage) 1-isostearylglycerol-3-phosphate: 85.5% 1-isostearyl-2-(3'-isostearylglyceroyl)glycerol-3-phosphate: 12.8% 1-isostearyl-2-(3'-isostearyl-2'-(3"-isostearyl glyceroyl)glyceroyl)glycerol-3-phosphate: 1.7%

IR (cm$^{-1}$, KBr-tablet method): 3424, 2928, 2860, 1470, 1380, 1124, 1060

Phosphorus content (elemental analysis): 6.3% Aluminum content (ICP analysis: inductively coupled plasma emission spectrometry): 2.6% Sodium content (atomic absorption spectrometry): 0.77% m=0.5 n=0.18

Manufacturing Example 3

Manufacturing of 1-isostearylglycerol-3-phosphate aluminum salt (3):

In an ethanol-hexane mixed solvent 72.1 g of 1-isostearylglycerol-3-phosphate obtained in Manufacturing Example 1 was dissolved, followed by the gradual addition of 26.65 g (0.153 mol) of L-arginine at 50° C. and stirred at 70° C. for 2 hours. Insoluble substances were removed by filtration. Subsequently, the filtrate was added gradually to acetone cooled down to 10° C. or less to precipitate white powder, which was then washed with acetone and dried to yield 61.3 g of 1-isostearylglycerol-3-phosphate monoarginate salt.

IR (cm$^{-1}$, KBr-tablet method): 3380, 2928, 2860, 1676, 1642, 1470, 1082, 936 NMR ($\delta$, ppm, D$_2$O-CD$_3$OD): 3.96-3.49, 3.23, 1.90, 1.74-1.14, 0.88

In 1120 g of ion-exchanged water 61.3 g of the above-obtained monoarginate salt was dissolved, followed by the addition, while stirring, of 17.86 g (0.103 mole) of L-arginine at 70° C. and further stirring for 30 minutes. Subsequently, a solution of 23.6 g (0.037 mole) of aluminum sulfate 14-18 hydrate dissolved in 66.4 g of water at 70° C. was added and stirred at 70° C. for 1 hour. After that, the resultant white precipitate was collected by filtration, then washed with water and dried to yield 47.3 g of 1-isostearylglycerol-3-phosphate aluminum salt. IR (cm$^{-1}$, KBr-tablet method): 3424, 2928, 2860, 1470, 1380, 1124, 1060 Phosphorus content (elemental analysis): 6.0% Aluminum content (ICP spectrometry): 4.1% m=0.66 n=0

Test Example 1

Solubility in Oily Materials

Solubilities of an aluminum salt, a sodium salt, a potassium salt and an arginine salt of 1-isostearylglycerol-3-phosphate in various oily materials were studied. That is, 3 g of each test compound was mixed with 30 ml of each of the oily materials and stirred at room temperature for 30 minutes, and then solubility was observed. The results are shown in Table 1. The term "soluble" is defined as the state that the mixture is homogeneous and not turbid without substantially any undissolved residue, and "insoluble" is defined as the state that the mixture is not homogeneous and is turbid.

In Table 1, Na salt, K salt, arginine salt and Al salt mean sodium salt, potassium salt, arginine salt and aluminum salt (Manufacturing Example 2) of 1-isostearylglycerol-3-phosphate, respectively.

TABLE 1

| Solvent | Test Compound | | | | | |
|---|---|---|---|---|---|---|
| | Al salt (Mfg. Ex. 1) | Al salt (Mfg. Ex. 2) | Al salt (Mfg. Ex. 3) | K salt | Na salt | Arginine salt |
| Isotridecyl isononanoate (Salacos 913 from The Nisshin Oil Mills, Ltd.) | Soluble | Soluble | Soluble | Insoluble | Insoluble | Insoluble |
| Alkyl-1,3-dimethyl butyl ether (ASE-166 from Kao Corp.) | Soluble | Soluble | Soluble | Insoluble | Insoluble | Insoluble |
| Polyglyceryl diisostealate (Cosmol 42 from The Nisshin Oil Mills, Ltd.) | Soluble | Soluble | Soluble | Insoluble | Insoluble | Insoluble |
| Glyceryl myristate isostearate (Exceparl DG-MI from Kao Corp.) | Soluble | Soluble | Soluble | Insoluble | Insoluble | Insoluble |
| Neopentyl dicaprate (Estemol N-01 from The Nisshin Oil Mills, Ltd.) | Soluble | Soluble | Insoluble | Insoluble | Insoluble | Insoluble |
| Glycol squalane (Nikkol Squalane from Nikko Chem. Co., Ltd.) | Soluble | Soluble | Insoluble | Insoluble | Insoluble | Insoluble |
| Water | Insoluble | Insoluble | Insoluble | Soluble | Soluble | Soluble |

Test Example 2

A model milky lotion containing a test compound was applied on the buccal region of the faces of normal healthy men (7 persons) twice a day for 6 weeks. In consequence, a pore-contracting effect was observed on 5 persons out of 7 for a milky lotion containing 2% by weight of the compound obtained in Manufacturing Example 2.

The invention claimed is:

1. A phosphorylated glyceryl ether aluminum salt represented by the general formula (1):

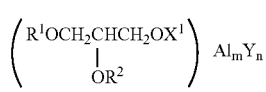

$$\left( \begin{array}{c} R^1OCH_2CHCH_2OX^1 \\ | \\ OR^2 \end{array} \right) Al_mY_n \quad (1)$$

wherein $R^1$ represents an alkyl or an alkenyl group with 8 to 32 carbon atoms; $R^2$ represents a hydrogen atom, a phosphoric acid residue or $—CH_2CH(OR^2)CH_2OR^1$, wherein $R^1$ and $R^2$ are the same as described above, provided that a repeated binding number is 4 at the most when $R^2$ is $—CH_2CH(OR^2)CH_2OR^1$; $X^1$ represents a hydrogen atom or a phosphoric acid residue; at least one of $X^1$ and $R^2$ is a phosphoric acid residue; Y represents an alkali metal atom or an alkaline earth metal atom; m represents a number from 0.3 to 1; and n represents a number from 0 to 1.

2. The compound of claim 1, wherein $R^1$ is an alkyl or an alkenyl group having a straight or a branched chain with 10 to 22 carbon atoms.

3. The compound of claim 1, wherein $R^1$ is a branched alkyl group with 10 to 22 carbon atoms.

4. The compound of claim 1, wherein said compound is 1-isostearylglycerol-3-phosphate aluminum salt.

5. An external dermatological agent, comprising:
the compound of claim 1; and
an oily material.

* * * * *